United States Patent
Bogdan et al.

(10) Patent No.: US 6,777,382 B2
(45) Date of Patent: Aug. 17, 2004

(54) COMPOSITIONS OF HYDROFLUOROCARBONS AND METHANOL

(75) Inventors: Mary C. Bogdan, Buffalo, NY (US); Kane D. Cook, Eggertsville, NY (US); Hang T. Pham, Amherst, NY (US); Gary M. Knopeck, Lakeview, NY (US); Rajiv R. Singh, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/160,900

(22) Filed: Jun. 3, 2002

(65) Prior Publication Data

US 2002/0198274 A1 Dec. 26, 2002

Related U.S. Application Data

(60) Provisional application No. 60/295,185, filed on Jun. 1, 2001.

(51) Int. Cl.$^7$ .............................................. C11D 17/00
(52) U.S. Cl. .................... 510/408; 62/114; 134/10; 134/21; 134/22.12; 134/22.14; 134/42; 252/182.24; 252/182.27; 510/412; 510/415; 521/50; 521/117; 521/131; 521/170
(58) Field of Search ........................ 521/50, 131, 117, 521/170; 510/408, 412, 415; 62/114; 134/10, 21, 22.12, 22.14, 42; 252/182.24, 182.27

(56) References Cited

U.S. PATENT DOCUMENTS

| | | | |
|---|---|---|---|
| 2,834,748 A | | 5/1958 | Bailey et al. |
| 2,846,458 A | | 8/1958 | Haluska |
| 2,917,480 A | | 12/1959 | Bailey et al. |
| 5,478,492 A | * | 12/1995 | Barthelemy et al. ........ 510/177 |
| 5,611,210 A | | 3/1997 | Nimitz et al. |
| 5,919,395 A | * | 7/1999 | Bastin et al. .......... 252/182.24 |
| 6,197,233 B1 | * | 3/2001 | Mason et al. ............... 264/45.9 |
| 6,476,080 B2 | * | 11/2002 | Duffy et al. .................. 516/12 |

OTHER PUBLICATIONS

Saunders, J.H. and Frisch, K.C. "Polyurethanes Chemistry and Technology" *Interscience Publishers*, vol. XVI, Part 1, 219–223 & Part II, 193–201.

Acree, Jr., William E., "Thermodynamic Properties of Non-electrolyte Solutions" *Academic Press*, (1984) 90–97, 180–189.

Prausnitz, Lichtenthaler, Azevedo, "Molecular Thermodynamics of Fluid–Phase Equilibria" *Prentice–Hall, Inc.* (*second edition*), pp. 279–290.

* cited by examiner

*Primary Examiner*—John M. Cooney, Jr.
(74) *Attorney, Agent, or Firm*—Deborah M. Chess

(57) ABSTRACT

The present invention provides compositions comprising an HFC component and a non-HFC component consisting essentially of methanol, having boiling points that are unexpectedly low and relatively constant, and uses thereof.

13 Claims, 1 Drawing Sheet

Figure 1:
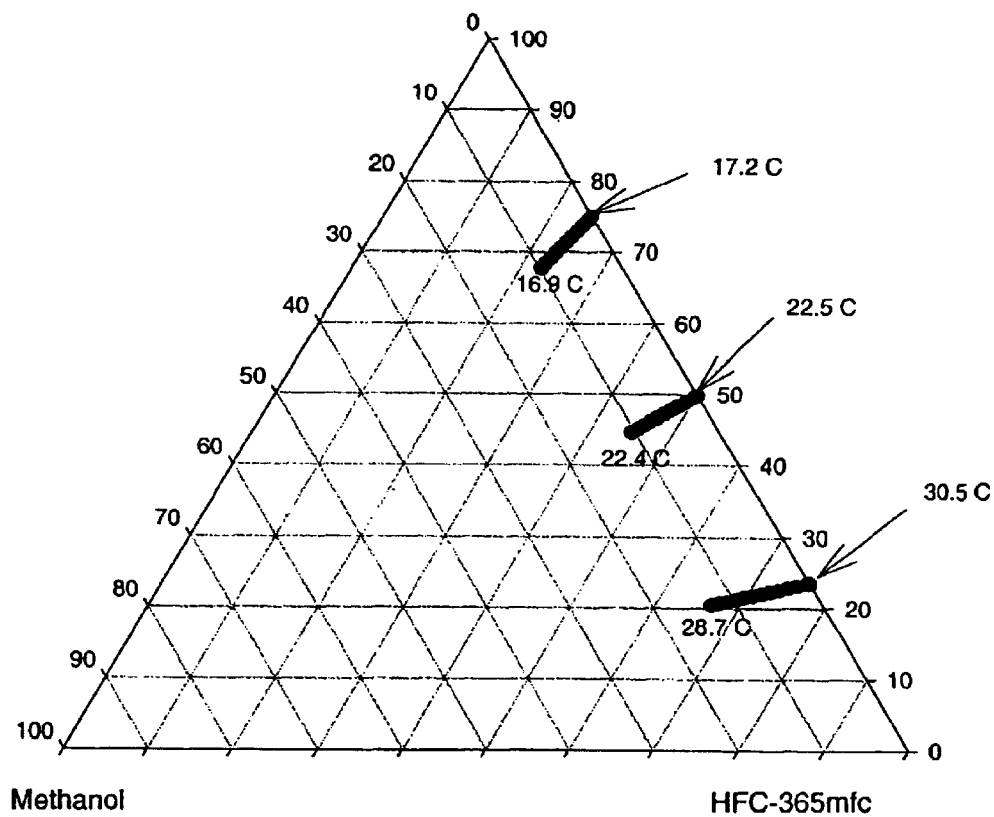

Ternary Plot of Boiling Points
HFC-245fa

COMPOSITIONS OF HYDROFLUOROCARBONS AND METHANOL

This applications claims the benefit of Provisional Application No. 60/295,185, filed Jun. 1, 2001.

FIELD OF INVENTION

The present invention relates generally to compositions comprising a hydrofluorocarbon ("HFC") component and a non-HFC component. More specifically, the present invention relates to ranges of HFC/methanol compositions having boiling points that are unexpectedly low and relatively constant, and uses thereof.

BACKGROUND

Hydrofluorocarbon-based compositions are of interest for use as replacements for chlorofluorocarbon ("CFC") and/or hydrochlorofluorocarbon ("HCFC") compositions, which tend to be environmentally undesirable. In particular, applicants have recognized that compositions comprising mixtures of hydrofluorocarbon ("HFC") are of interest for use in a wide range of applications, including for use as propellants in aerosol or other sprayable compositions. Unfortunately, applicants have identified a number of disadvantages associated with adapting HFCs for use in aerosols.

One such disadvantage is an HFC's insolubility with many of the lubricants used commonly in refrigeration and spraying applications. Applicants recognize, however, that mixing the HFC with certain non-HFCs solublizing agents can improve the composition's solubility with such lubricants. In such embodiments, it is highly advantageous, if not necessary, for HFC/non-HFC compositions to be soluble with lubricants which are used in conventional CFC applications such as CASTROL SW2 Polyol ester refrigerant oil and LUBRIKUHL 130 ESTER Polyol ester refrigerant oil.

Although mixing an HFC with a particular non-HFC tends to improve its solubility, the introduction of the particular non-HFC also tends to have negative consequences. First, the non-HFC increases the flammability of the composition. Applicants have come to appreciate that solubility and flammability are often competing requirements since components of a composition which tend to increase solubility with lubricants oils also tend to increase the flammability of such compounds. Therefore, there is a need for HFC/non-HFC mixtures that are not only sufficiently soluble in conventional lubricants, but also are relatively non-flammable.

In addition to flammability, the non-HFC component tends to increase the sensitivity of the composition's boiling point to compositional changes. Conventional aerosol cans and other sprayers known in the art are designed to work with fluids having a specific vapor pressure and boiling point. If the vapor pressure/boiling point characteristics of a fluid to be sprayed are different from the specific characteristics for which the sprayer has been designed, the sprayer will not work. For example, in certain cases, a sprayer designed to work with a composition of having a boiling point of 50° C., will often not work with a composition having a boiling point that differs by as little as 1° C. or more.

Unfortunately, as is known in the art, the combination of two or more constituents to form an HFC/non-HFC composition often results in compositions wherein relatively small changes in the relative concentrations of the components result in relatively large changes in boiling point and vapor pressure. For example, if a non-HFC has a higher boiling point than the HFC (which is likely when the non-HFC is a solublizing agent), then it is generally understood that the boiling point of the HFC/non-HFC composition will increase as the concentration of the non-HFC component is increased. This increase in boiling can be significant, especially if the non-HFC component has a high boiling point. Accordingly, relatively small changes in the relative concentration of components in a composition may have a relatively large effect on the composition's boiling point. As mentioned above, spraying and refrigeration apparatus are generally intolerant of changes in the boiling point of the compositions used therewith.

In light of the above, applicants recognize that HFC mixtures having a relatively constant boiling point, that is, a boiling point which changes by a relatively small amount as the relative concentrations of the components change, are desirable. Specifically, a relatively constant boiling point/vapor pressure, would facilitate the use of a wide range of compositions with relatively few number of spraying devices. Unfortunately, HFC/non-HFC mixtures having such relatively constant boiling point properties are uncommon and unpredictable.

Therefore, there is a need for a HFC mixture which is soluble with lubricants while being non-flammable and having a relatively constant boiling point across a range of varying constituent concentrations. The present invention fulfills this need among others.

DETAILED DESCRIPTION OF PREFERRED EMBODIMENT

The present invention overcomes the aforementioned shortcomings by providing for HFC compositions that are not only soluble in conventional lubricants, but also exhibit a relatively constant boiling point and are non-flammable. Specifically, the applicants have identified a composition comprising an HFC component, namely a mixture of 1,1,1, 3,3-pentafluorobutane ("HFC-365mfc") and 1,1,1,3,3-pentafluoropropane ("HFC-245fa"), and a non-HFC solublizing agent, namely, methanol.

This composition has a remarkably steady boiling point with respect to compositional changes and even displays "quasi-azeotropic" characteristics. As used herein, the term "quasi-azeotropic" refers to a characteristic of a mixture in which its boiling point falls outside the highest and lowest boiling points of the composition's HFC component and non-HFC component. In the present invention, the composition has a boiling point which is below the boiling point of both the HFC component (i.e. the mixture of HFC-365mfc and HFC-245fa) and the non-HFC component (i.e., the methanol). This is surprising, especially when one considers the fact that the boiling point of methanol is well above the boiling points of either HFC-365mfc or HFC-245fa. It should be understood that even though the composition of the present invention has a boiling point below the HFC component, it does not necessarily have a boiling point below each of the HFCs in the HFC component (i.e., HFC-365mfc and HFC-245fa individually). Indeed, in this case, the composition does not have a boiling point below HFC-245fa-hence, its characterization as a quasi-azeotrope rather than an azeotrope.

Without being bound or limited by any particular theory, applicants suspect that the the quasi-azeotropic characteristics of the composition tend to stabilize, to some degree, the relative concentration of the components in the composition during vaporization. More specifically, since the composition has a boiling point lower than the HFC and non-HFC components, there may be a tendency during vaporization for the relative concentration of the components to gravitate toward a particular relationship in which the composition has the lowest boiling point. At this point, vaporizing the composition should have relatively little impact on the relative concentrations of the HFC and non-HFC components-i.e., the composition will manifest azeotropic characteristics. As is well known, if the relative concentration of the components is stable during vaporization, the boiling point of the composition will be stable.

It should be understood, however, that the composition of the present invention will not behave as a true azeotrope since the HFC-245fa constituent of the HFC component has a lower boiling point than that of the composition. Accordingly, as the composition vaporizes HFC-245fa will vaporize at a higher rate and thereby change the relative concentration of the HFC component. A change in the relative concentration of the HFC component will affect the relative concentration of the HFC and non-HFC components, which, in turn, will affect the boiling point of the composition. It is suspected, however, that this affect on boiling point will be tempered in good measure by the the quasi-azeotropic characteristics of the composition.

Aside from the quasi-azeotropic chartacteristics of the composition, applicants have also observed that the composition has a relatively constant boiling point. As used herein, the term "relatively constant boiling point composition" refers generally to a composition, comprising two or more constituents in which a relative change in the composition's constituents results in a less than expected change in the boiling point of the composition. Most compositional boiling points can be predicted using a number of techniques known in the art. Perhaps the most common approach is by using the Regular Solution Model (illustrated in Acree, Jr., "Thermodynamic Properties of Nonelectrolyte Solutions", Academic Press (1984) 90–97, 180–189 and Prausnitz, Lichtenthaler, Azevedo "Molecular Thermodynamics of Fluid-Phase Equilibria", Prentice-Hall, Inc. (second edition), pp. 279–290, both of which are incorporated herein by reference). For purposes of explanation and simplicity, any reference herein to "expected" boiling points, changes therein, or data therefor can be assumed to be calculated using the Regular Solution Model unless otherwise stated. Any composition wherein the change in boiling point is less than predicted is considered a relatively-constant-boiling-point composition for purposes of the present invention.

Applicants discovered unexpectedly that the composition of the present invention is a relatively-constant-boiling-point compositions. Furthermore, despite the relatively higher amounts of flammable methanol present in the instant compositions, applicants have discovered unexpectedly that such compositions are relatively low to non-flammable. Applicants have measured the flammability of the compositions of the present invention using a watchglass flammability test, wherein a given amount of composition is placed in a watch glass and a flame is introduced above the glass, and discovered that compositions containing as much as 10 wt. % methanol or more are non-flammable.

In a preferred embodiment, the composition consists essentially of the HFC and non-HFC components. The concentration of the non-HFC component in the composition is, preferably, from greater than 0 to about 13 wt. %, more preferably, from about 1 to about 10 wt. %, even more preferably, from about 1 to about 6 wt. %, and, still more preferably, from about 2 to about 5 wt. %.

The relative concentration of HFC-365mfc and HFC-245fa in the HFC component can vary according to the application and can be optimized by one skilled in the art. For example, suitable results have been obtained using HFC-365mfc:HFC-245fa concentration (wt. %) ratios of 25:75, 50:50, and 75:25.

Uses of the Compositions

The present compositions have utility in a wide range of applications. For example, one embodiment of the present invention relates to the use of the present compositions as propellants/solvents in sprayable compositions. In general, sprayable-type compositions comprise a material to be sprayed and a propellant/solvent or mixture of propellant solvents. For the sprayable compositions to be useful, it is necessary that the material to be sprayed be relatively or substantially soluble in the propellant/solvents to be used. While many HFCs are poor solvents for many conventional sprayable materials, applicants have recognized that the compositions of the present invention exhibit relatively high solubility with such materials, while also remaining non-flammable.

Any of a wide range of sprayable materials can be used in conjunction with the compositions of the present invention to produce the instant sprayable compositions. Examples of suitable materials include, without limitation, oils and other lubricants, release agents, cleaners, polishing agents, medicinal materials, such as, anti-asthma and anti-halitosis medicines, as well as, cosmetic materials, such as, deodorants, perfumes, hair sprays, and the like.

The sprayable compositions of the present invention may further comprise any of a wide range of inert ingredients, additional solvents, and other materials used conventionally in sprayable compositions.

In other embodiments, the compositions of the present invention are used as refrigerants in any of a wide variety of refrigeration systems. In certain preferred embodiments, the compositions of the present invention may be used in refrigeration systems containing a lubricant used conventionally with CFC-refrigerants, such as mineral oils, silicone oils, and the like. While HFC-containing refrigerants tend to be poorly soluble with conventional refrigeration lubricants, and therefore tend to be incompatible with such lubricants, applicants have recognized that the relative solubility of the present compositions makes them suitable, and in some cases, ideal candidates for use with conventional lubricants.

In addition, the relatively constant boiling nature of the compositions of the present invention makes them even more desirable for use as refrigerants in many applications.

In certain embodiments, the compositions of the present invention may be used to retrofit refrigeration systems containing CFC-refrigerants and conventional lubricants. Preferably, the present methods involve recharging a refrigerant system that contains a chlorine-containing refrigerant and a lubricant comprising the steps of (a) removing the chlorine-containing refrigerant from the refrigeration system while retaining a substantial portion of the lubricant in said system; and (b) introducing to the system a composition of the present invention. As used herein, the term "substantial portion" refers generally to a quantity of lubricant which is at least about 50% (by weight) of the quantity of lubricant contained in the refrigeration system prior to removal of the chlorine-containing refrigerant. Preferably, the substantial portion of lubricant in the system according to the present invention is a quantity of at least about 60% of the lubricant contained originally in the refrigeration system, and more preferably a quantity of at least about 70%. As used herein the term "refrigeration system" refers generally to any system or apparatus, or any part or portion of such a system or apparatus, which employs a refrigerant to provide cooling. Such refrigeration systems include, for example, air conditioners, electric refrigerators, chillers, transport refrigeration systems, commercial refrigeration systems and the like.

Those of skill in the art will recognize that the refrigeration systems used in the methods of the present invention generally comprise a chamber in which both a refrigerant and lubricant are contained and through which the refrigerant and lubricant can be circulated. According to certain embodiments of the present invention, the removal step (a) comprises removing a chlorine-containing refrigerant from a refrigeration system, especially from a chamber within the system, while leaving a substantial amount of lubricant, and preferably a hydrocarbon-based lubricant, in the system.

Any of a wide range of known methods can be used to remove chlorine-containing refrigerants from a refrigeration system while removing less than a major portion of the lubricant contained in the system. According to preferred embodiments, the lubricant is a hydrocarbon-based lubricant and the removal step results in at least about 90%, and even more preferably at least about 95%, of said lubricant remaining in the system. For example, because refrigerants are quite volatile relative to traditional hydrocarbon-based lubricants (the boiling points of refrigerants are generally less than 10° C. whereas the boiling points of mineral oils are generally more than 200° C.), the removal step may readily be performed by pumping chlorine-containing refrigerants in the gaseous state out of a refrigeration system containing liquid state lubricants. Such removal can be achieved in any of a number of ways known in the art, including, the use of a refrigerant recovery system, such as the recovery system manufactured by Robinair of Ohio. Alternatively, a cooled, evacuated refrigerant container can be attached to the low pressure side of a refrigeration system such that the gaseous refrigerant is drawn into the evacuated container and removed. Moreover, a compressor may be attached to a refrigeration system to pump the refrigerant from the system to an evacuated container. In light of the above disclosure, those of ordinary skill in the art will be readily able to remove chlorine-containing lubricants from refrigeration systems and to provide a refrigeration system comprising a chamber having therein a hydrocarbon-based lubricant and substantially no chlorine-containing refrigerant according to the present invention.

Any of a wide range of methods for introducing the refrigerant composition to a refrigeration system comprising a hydrocarbon-based lubricant can be used in the present invention. For example, one method comprises attaching a refrigerant container to the low-pressure side of a refrigeration system and turning on the refrigeration system compressor to pull the refrigerant into the system. In such embodiments, the refrigerant container may be placed on a scale such that the amount of refrigerant composition entering the system can be monitored. When a desired amount of refrigerant composition has been introduced into the system, charging is stopped. Alternatively, a wide range of charging tools, known to those of skill in the art, is commercially available. Accordingly, in light of the above disclosure, those of skill in the art will be readily able to introduce non-chlorine compositions into refrigeration systems according to the present invention without undue experimentation.

In still other embodiments, the present invention provides foamable compositions, and preferably polyurethane and polyisocyanurate foam compositions, and methods of preparing foams. In such foam embodiments, one or more of the present compositions are included as a blowing agent in a foamable composition, which composition preferably includes one or more additional components capable of reacting and foaming under the proper conditions to form a foam or cellular structure, as is well known in the art. The present methods preferably comprise providing such a foamable composition and reacting it under conditions effective to obtain a foam, and preferably a closed cell foam. The invention also relates to foam, and preferably closed cell foam, prepared from a polymer foam formulation containing a blowing agent comprising the composition of the invention.

Any of the methods well known in the art, such as those described in "Polyurethanes Chemistry and Technology," Volumes I and II, Saunders and Frisch, 1962, John Wiley and Sons, New York, N.Y., which is incorporated herein by reference, may be used or adapted for use in accordance with the foam embodiments of the present invention. In general, such preferred methods comprise preparing polyurethane or polyisocyanurate foams by combining an isocyanate, a polyol or mixture of polyols, a blowing agent or mixture of blowing agents comprising one or more of the present compositions, and other materials such as catalysts, surfactants, and optionally, flame retardants, colorants, or other additives. It is convenient in many applications to provide the components for polyurethane or polyisocyanurate foams in pre-blended formulations. Most typically, the foam formulation is pre-blended into two components. The isocyanate and optionally certain surfactants and blowing agents comprise the first component, commonly referred to as the "A" component. The polyol or polyol mixture, surfactant, catalysts, blowing agents, flame retardant, and other isocyanate reactive components comprise the second component, commonly referred to as the "B" component. Accordingly, polyurethane or polyisocyanurate foams are readily prepared by bringing together the A and B side components either by hand mix for small preparations and, preferably, machine mix techniques to form blocks, slabs, laminates, pour-in-place panels and other items, spray applied foams, froths, and the like. Optionally, other ingredients such as fire retardants, colorants, auxiliary blowing agents, and even other polyols can be added as a third stream to the mix head or reaction site. Most conveniently, however, they are all incorporated into one B-component as described above.

Dispersing agents, cell stabilizers, and surfactants may also be incorporated into the blowing agent mixture. Surfactants, better known as silicone oils, are added to serve as cell stabilizers. Some representative materials are sold under the names of DC-193, B-8404, and L-5340 which are, generally, polysiloxane polyoxyalkylene block co-polymers such as those disclosed in U.S. Pat. Nos. 2,834,748, 2,917,480, and 2,846,458. Other optional additives for the blowing agent mixture may include flame retardants such as tri(2-chloroethyl)phosphate, tri(2-chloropropyl)phosphate, tri(2,3-dibromopropyl)-phosphate, tri(1,3-dichloropropyl) phosphate, diammonium phosphate, various halogenated aromatic compounds, antimony oxide, aluminum trihydrate, polyvinyl chloride, and the like.

Generally speaking, the amount of blowing agent present in the blended mixture is dictated by the desired foam densities of the final polyurethane or polyisocyanurate foams products. The proportions in parts by weight of the total blowing agent or blowing agent blend can fall within the range of from 1 to about 60 parts of blowing agent per 100 parts of polyol. Preferably from about 10 to about 35 parts by weight of the present composition per 100 parts by weight of polyol are used.

The components of the composition of the invention are known materials that are commercially available or may be prepared by known methods. Preferably, the components are of sufficiently high purity so as to avoid the introduction of adverse influences upon cooling or heating properties, constant boiling properties, or blowing agent properties of the system. In the case of metered dose inhalers, the relevant current Good Manufacturing Process may be used for manufacturing these materials.

Additional components may be added to tailor the properties of the compositions of the invention as needed. By way of example, oil solubility aids may be added in the case in which the compositions of the invention are used as refrigerants. Stabilizers and other materials may also be added to enhance the properties of the compositions of the invention.

EXAMPLES

Example 1

Three HFC component samples A, B, and C consisting of HFC-365mfc and HFC-245fa are prepared. Sample A is prepared using about 10 g HFC-365mfc and about 30 g HFC-245fa, Sample B is prepared using about 20 g HFC-365mfc and about 20 g HFC-245fa, and Sample C is prepared using about 30 g HFC-365mfc and about 10 g HFC-245fa. Each sample is tested for azeotrope-like properties as described below.

An ebulliometer consisting of vacuum jacketed tube with a condenser on top is used. A component sample is charged to the ebulliometer at the pressure indicated in Table 1 and then methanol is added in small, measured increments. Temperature depression is observed when methanol is added to the sample, indicating an azeotrope-like composition is formed between the sample composition and methanol. From about 1 to about 13 weight percent of methanol, the boiling point of the sample/methanol composition changes by about 3° C. or less.

Tables 1, 2 and 3 show the compositions tested (for samples A, B, and C, respectively) and the boiling points associated therewith. FIG. 1 is a ternary plot of the boiling points listed in Tables 1, 2 and 3 for the compositions.

TABLE 1

| Wt. % 365 mfc | Wt. % 245 fa | Wt. % MeOH | Tb C |
|---|---|---|---|
| 25.00 | 75.00 | 0.00 | 17.2 |
| 24.86 | 74.58 | 0.56 | 17.1 |
| 24.58 | 73.75 | 1.67 | 16.5 |
| 24.31 | 72.93 | 2.76 | 16.5 |
| 24.05 | 72.14 | 3.82 | 16.4 |
| 23.79 | 71.36 | 4.86 | 16.5 |
| 23.53 | 70.60 | 5.87 | 16.6 |
| 23.28 | 69.85 | 6.87 | 16.7 |
| 23.04 | 69.12 | 7.84 | 16.8 |
| 22.80 | 68.41 | 8.79 | 16.8 |
| 22.57 | 67.71 | 9.73 | 16.9 |

Atm pressure 14.49 psia

TABLE 2

| Wt. % 365 mfc | Wt. % 245 fa | Wt. % MeOH | Tb C |
|---|---|---|---|
| 50.20 | 49.80 | 0.00 | 22.5 |
| 49.90 | 49.50 | 0.61 | 22.3 |
| 49.30 | 48.90 | 1.80 | 21.4 |
| 48.71 | 48.33 | 2.96 | 21.4 |
| 48.14 | 47.76 | 4.10 | 21.7 |
| 47.59 | 47.21 | 5.21 | 22.1 |
| 47.04 | 46.67 | 6.29 | 22.1 |
| 46.51 | 46.14 | 7.35 | 22.1 |
| 45.99 | 45.62 | 8.39 | 22.1 |
| 45.48 | 45.12 | 9.40 | 22.4 |
| 44.98 | 44.63 | 10.39 | 22.4 |

Atm pressure 14.46 psia

TABLE 3

| Wt. % 365 mfc | Wt. % 245 fa | Wt. % MeOH | Tb C |
|---|---|---|---|
| 76.5 | 23.5 | 0.00 | 30.5 |
| 76.25 | 23.42 | 0.33 | 30.1 |
| 75.27 | 23.11 | 1.63 | 27.6 |
| 74.29 | 22.82 | 2.89 | 28.7 |
| 73.35 | 22.53 | 4.12 | 28.7 |
| 72.43 | 22.25 | 5.32 | 28.2 |
| 71.54 | 21.97 | 6.49 | 28.4 |
| 70.66 | 21.71 | 7.63 | 28.6 |
| 69.81 | 21.45 | 8.74 | 28.6 |
| 68.98 | 21.19 | 9.83 | 28.7 |
| 68.17 | 20.94 | 10.89 | 28.7 |
| 67.37 | 20.70 | 11.93 | 28.7 |

TABLE 3-continued

| Wt. % 365 mfc | Wt. % 245 fa | Wt. % MeOH | Tb C |
|---|---|---|---|
| 66.60 | 20.46 | 12.94 | 28.7 |
| | | | Atm pressure 14.57 psia |

Example 2

This example illustrates the solubility of various lubricants in the compositions of this invention.

To a clear glass vial is added a composition of the present invention to be tested and the weight of the mixture was determined. A conventional lubricant, i.e. one listed in Table 4, is added at room temperature. The vial is sealed and shaken gently. The mixture is then observed. The presence of turbidity and/or of two distinct phases indicates that the lubricant is insoluble in the solvent. A single-phase, homogeneous system indicates miscibility. The solubilities of various conventional lubricants is shown in table 4.

TABLE 4

| OIL or LUBRICANT | WT % SOLUBILITY |
|---|---|
| CASTROL SW2 Polyol ester refrigerant oil (CASTROL) | SOLUBLE >5.0 WT. % |
| LUBRIKUHL 130 ESTER Polyol ester refrigerant oil (LUBRIZOL) | SOLUBLE >5.0 WT. % |
| MOBIL EAL 22 Polyol ester refrigerant oil (MOBIL/EXXON) | SOLUBLE >5.0 WT. % |
| PAG PYROIL Polyalkyl glycol refrigerant oil (UNION CARBIDE) | SOLUBLE >5.0 WT. % |
| FOMBLIN AM 3001 perfluorinated oil (AUSIMONT) | SOLUBLE >5.0 WT. % |
| FOMBLIN 2001 perfluorinated oil (AUSIMONT) | SOLUBLE >5.0 WT. % |
| LD-4 (tributyl phosphate containing) Hydraulic fluid (SKYDROL) | SOLUBLE >5.0 WT. % |
| FS-1265 fluid (300 centistokes.) Fuorosilicone fluid (DOW CORNING) | SOLUBLE >5.0 WT. % |

Example 3

One hundred (100) g of a polyether having a hydroxyl value of 380, a result from the addition of propylene oxide to a solution of saccharose, propylene glycol and water, is mixed with 2 g of a siloxane polyether copolymer as foam stabilizer, and 3 g of dimethylcyclohexylamine. With stirring, 100 g of the mixture is thoroughly mixed with 15 g of a composition of the present invention as a blowing agent. The resulting mixture is foamed with 152 g of crude 4,4' diisocyanatodiphenylmethane. The resulting rigid foam is inspected and found to be of good quality.

Example 4

This example shows that foams prepared using the azeotrope-like compositions described in this invention as foam blowing agents exhibit improved k-factors. In general the formulations used to prepare these foams are described in Table 5.

TABLE 5

| Component (pbw) | |
|---|---|
| Terate 2541[1] | 100.00 |
| Tegostab B8433[2] | 2.00 |
| Polycat 8[3] | 0.25 |
| Dabco K-15[3] | 2.80 |
| blend of present HFC component and methanol | 38.00 |
| Lupranate M70L[4] | 150.10 |
| Index | 250 |

[1]Polyol from COSA; hydroxyl number = 240
[2]Surfactant from GoldschmidtChemical Company
[3]Catalyst from Air Products & Chemicals Inc.
[4]A Polymethylene poly(phenyl isocyanate) mixture containing about 40% by weight of methylenebis(phenyl isocyanate) with the balance being polymethylene poly(phenyl isocyanate) having a functionality greater than 2; isocyanate equivalent weight = about 134; from BASF Corp.

The general procedure commonly referred to as "hand-mixing" is used to prepare all foams. For each blowing agent or blowing agent pair, a premix of polyol, Terate 2541, surfactant, Tegostab B8433, and catalyst, Dabco K-15 and Polycat 8, is prepared in the same proportions displayed in Table 2. About 2 kg is blended to insure that all of the foams in a given series are made with the same master batch of premix. The premix is blended in a one-gallon paint can, and stirred at about 1500 rpm with a Conn 2" diameter ITC mixer until a homogenous blend is achieved. When mixing was complete the material is transferred to a one-gallon glass bottle and sealed. The bottle is then placed in a refrigerator controlled at 50° F. The foam blowing agents are premixed and kept in the a refrigerator, along with the 32 oz. tin cans used for mixing vessels. The A-component, isocyanate, is kept in sealed containers at 70° F.

For the individual foam preparations, an amount of B-component equal to the formulation weight is weighted into a 32 oz. tin can preconditioned at 50° F. To this is added the required amount of the blowing agent blend, also pre-conditioned to 50° F. The contents are stirred for two-minutes with a Conn 2" ITC mixing blade turning at about 1000 rpm. Following this, the mixing vessel and contents are reweighed. If there is a weight loss, the lower boiling blowing agent is added to make up the loss. The contents are stirred for an additional 30 seconds, and the can is replaced in the refrigerator.

After the contents are cooled again to 50° F., approximately 10 minutes, the mixing vessel is removed from the refrigerator and taken to the mixing station. A pre-weighed portion of A-component, isocyanate, is added quickly to the B-component, the ingredients mixed for 10 seconds using a Conn 2" diameter ITC mixing blade at 3000 rpm and poured into a 8"×8"×4" cardboard cake box and allowed to rise. Cream, initiation, gel and tack free times are recorded for the individual polyurethane foam samples.

The foams are allowed to cure in the boxes at room temperature for at least 24 hours. After curing, the blocks are trimmed to a uniform size and densities measured. Any foams that do not meet the density specification 2.0±0.1 lb/ft 3 are discarded, and new foams prepared using an adjusted amount of blowing agent in the formulation to obtain the specified density.

After ensuring that all the foams meet the density specifications, the foams are tested for k-factor according to ASTM C518. The resulting rigid foam is inspected and found to be of good quality.

What is claimed is:

1. A composition comprising:
   an HFC component consisting essentially of 1,1,1,3,3-pentafluorobutane and 1,1,1,3,3-pentafluoropropane; and
   from about 1 to about 13 weight percent of the composition of a non-HFC component consisting essentially of methanol.

2. The composition of claim 1, wherein said HFC component has a first boiling point at a given pressure and said non-HFC component has a second boiling point at said given pressure, and wherein said composition has a boiling point at said given pressure which is lower than said first and second boiling points.

3. The composition of claim 1, wherein said non-HFC component consists essentially of from about 1 to about 10 weight percent methanol.

4. The composition of claim 1, wherein said non-HFC component consists essentially of from about 1 to about 6 weight percent methanol.

5. The composition of claim 1, wherein said non-HFC component consists essentially of from about 2 to about 5 weight percent methanol.

6. A composition according to claim 1 wherein said composition is non-flammable.

7. A sprayable composition comprising a material to be sprayed and a propellant comprising a composition according to claim 1.

8. A refrigerant composition comprising a composition according to claim 1.

9. A method for recharging a refrigerant system that contains a chlorine-containing refrigerant and a lubricant comprising the steps of:
   (a) removing the chlorine-containing refrigerant from the refrigeration system while retaining a substantial portion of the lubricant in said system; and
   (b) introducing to said system a composition according to claim 1.

10. A blowing agent comprising a composition according to claim 1.

11. A method for producing a foam comprising foaming a composition containing a composition according to claim 1.

12. A premix of a polyol and a blowing agent comprising a composition according to claim 1.

13. A closed cell foam composition prepared by foaming a foamable composition containing a composition according to claim 1.

* * * * *